US008022251B2

(12) United States Patent
McArdle et al.

(10) Patent No.: US 8,022,251 B2
(45) Date of Patent: Sep. 20, 2011

(54) IMINIUM SALTS AND METHODS OF PREPARING ELECTRON DEFICIENT OLEFINS USING SUCH NOVEL IMINIUM SALTS

(75) Inventors: Ciaran B. McArdle, Dublin (IE); Ligang Zhao, Goettingen (IE)

(73) Assignee: Loctite (R&D) Limited, Dublin (IE)

( * ) Notice: Subject to any disclaimer, the term of this patent is extended or adjusted under 35 U.S.C. 154(b) by 136 days.

(21) Appl. No.: 12/424,198

(22) Filed: Apr. 15, 2009

(65) Prior Publication Data
US 2009/0203934 A1 Aug. 13, 2009

Related U.S. Application Data

(63) Continuation of application No. PCT/IE2007/000104, filed on Oct. 25, 2007.

(60) Provisional application No. 60/862,819, filed on Oct. 25, 2006.

(51) Int. Cl.
*C07C 257/00* (2006.01)

(52) U.S. Cl. ........................................................ 564/278

(58) Field of Classification Search .................... 564/278
See application file for complete search history.

(56) References Cited

U.S. PATENT DOCUMENTS

| 2,582,128 | A | 1/1952 | Hurwitz |
| 2,721,858 | A | 10/1955 | Joyner et al. |
| 2,763,677 | A | 9/1956 | Jeremias et al. |
| 3,142,698 | A | 7/1964 | Halpern et al. |
| 3,903,055 | A | 9/1975 | Buck |
| 3,975,422 | A | 8/1976 | Buck |
| 4,003,942 | A | 1/1977 | Buck |
| 4,012,402 | A | 3/1977 | Buck |
| 4,013,703 | A | 3/1977 | Buck |
| 4,364,876 | A | 12/1982 | Kimura et al. |
| 4,587,059 | A | 5/1986 | Harth et al. |
| 5,455,369 | A | 10/1995 | Meier et al. |
| 5,624,699 | A | 4/1997 | Lang |
| 5,703,267 | A | 12/1997 | Takahashi et al. |
| 5,744,642 | A | 4/1998 | Lantzsch et al. |
| 6,096,848 | A | 8/2000 | Gololobov et al. |
| 6,245,933 | B1 | 6/2001 | Malofsky et al. |
| 7,569,719 | B1* | 8/2009 | McArdle et al. ............... 558/462 |
| 7,718,821 | B1* | 5/2010 | Bigi et al. ..................... 558/443 |

FOREIGN PATENT DOCUMENTS

WO WO03086605 10/2003

OTHER PUBLICATIONS

Buck, C. J., "Unequivocal Synthesis of Bis(2-Cyanoacrylate) Monomers. I. Via Anthracene Adducts", Journal of Polymer Science: Polymer Chemistry Edition, vol. 16, p. 2475-2507, 1978
Vijn, R. J., et al., "Synthesis of Alkyl- and Aryl-Substituted Pyridines from (α, β-Unsaturated) Imines or Oximes and Carbonyl Compounds", Synthesis, p. 573-578, Jun. 1994.
Davis, J. H., "Task-Specific Ionic Liquids", Chemistry Letters, vol. 33, No. 9, p. 1072-1077, 2004.
Smith, M. B., Organic Synthesis: Theory, Reactions, and Methods, p. 1302, 1994.
Tehrani, K. A., et al., "Product Class 8: Iminium Salts", Science of Synthesis, 27.8, p. 313-348, 2004.
Hin, B., et al., "Facile Synthesis of α-Substituted Acrylate Esters", J. Org. Chem., vol. 67, p. 7365-7368 2002.
Holy, N., et al., "The Mannich Reaction-II: Derivatization of Aldehydes and Ketones Using Dimethyl(Methylene)Ammonium Salts", Tetrahedron, vol. 35, p. 613-619, 1979.
Bryson, T. A., et al., "Preformed Mannich Salts: A Facile Preparation of Dimethyl(Methylene)Ammonium Iodine", J. Org. Chem., vol. 45, p. 524-525, 1980.
Jahn, U., et al., "A Novel and Simple Method For The Preparation of Iminium Salts", Tetrahedron Letters, vol. 34, No. 37, p. 5863-5866, 1993.
Davis, J. H., et al., "Synthesis and Purification of Ionic Liquids", Ionic Liquids in Synthesis, Chapter 2, 2002.
Kotzev, D. L., et al., "Synthesis and Properties of Some Alkenyl- and Alkinyl-2-Cyanoacrylates", Die Angewandte Makromlekulare Chemie, vol. 92, p. 41-52, 1980.
Cattoen, X., et al., "Transient Azomethine-Ylides From a Stable Amino-Carbene And an Aldiminium Salt", J. Org. Chem. , vol. 68, p. 911-914, 2003, XP002468031.
Volz, H., et al., "Methylenimmoniumsalze durch Hydrid-Abstrakction aus Tertiaren Aminen", Justus Liebigs Annalen Der Chemi, vol. 752, p. 86-101, 1971, XP002468032.

* cited by examiner

*Primary Examiner* — Rei-tsang Shiao
(74) *Attorney, Agent, or Firm* — Steven C. Bauman (57) ABSTRACT

This invention relates to novel iminium salts, which may be in the form of ionic liquids, and a process for producing electron deficient olefins, such as 2-cyanoacrylates, using such an iminium salt, for instance in the form of an ionic liquid.

12 Claims, 2 Drawing Sheets

FIG. 1

Reactions A, B, and C respectively

FIG. 2

IMINIUM SALTS AND METHODS OF PREPARING ELECTRON DEFICIENT OLEFINS USING SUCH NOVEL IMINIUM SALTS

BACKGROUND OF THE INVENTION

1. Field of the Invention

This invention relates to novel iminium salts, which may be in the form of ionic liquids ("ILs"), and a process for producing electron deficient olefins, such as 2-cyanoacrylates, using such an iminium salt, for instance in the form of an IL.

2. Brief Description of Related Technology

Cyanoacrylate adhesives are known for their fast adhesion and ability to bond a wide variety of substrates. They are marketed as "super glue" type adhesives. They are useful as an all-purpose adhesive since they are a single component adhesive, very economical as only a small amount will do, and generally do not require any equipment to effectuate curing.

Traditionally, cyanoacrylate monomers have been produced by way of a Knoevenaqel condensation reaction between a formaldehyde precursor, such as paraformaldehyde, and an alkyl cyanoacetate with a basic catalyst. During the reaction, cyanoacrylate monomer forms and polymerises in situ to a prepolymer. The prepolymer is subsequently thermally cracked or depolymerised, yielding cyanoacrylate monomer. This approach has remained essentially the same over time, though various improvements and variants have been introduced. See e.g. U.S. Pat. Nos. 6,245,933, 5,624,699, 4,364,876, 2,721,858, 2,763,677 and 2,756,251.

In U.S. Pat. No. 3,142,698, the synthesis of difunctional cyanoacrylates using a Knoevenagel condensation reaction is described. However, the ability to thermally depolymerise the resulting, now crosslinked, prepolymer in a reliable and reproducible manner to produce pure difunctional monomers in high yields is questionable [see J. Buck, *J. Polym. Sci., Polym. Chem. Ed.*, 16, 2475-2507 (1978), and U.S. Pat. Nos. 3,975,422, 3,903,055, 4,003,942, 4,012,402, and 4,013,703].

A variety of other processes for producing cyanoacrylate monomers are known, some of which are described below. For instance, U.S. Pat. No. 5,703,267 defines a process for producing a 2-cyanoacrylic acid which comprises subjecting a 2-cyanoacrylate and an organic acid to a transesterification reaction.

U.S. Pat. No. 5,455,369 defines an improvement in a process for preparing methyl cyanoacrylate, in which methyl cyanoacetate is reacted with formaldehyde to form a polymer that is then depolymerized to the monomeric product, and in which the purity of yield is 96% or better. The improvement of the '369 patent is reported to be conducting the process in a poly(ethylene glycol) diacetate, dipropionate, or dibutyrate, having a number average molecular weight of 200-400, as the solvent.

U.S. Pat. No. 6,096,848 defines a process for the production of a biscyanoacrylate, which comprises the steps of esterifying a 2-cyanoacrylic acid or transesterifying an alkyl ester thereof to obtain a reaction mixture; and fractionally crystallizing the reaction mixture to obtain the biscyanoacrylate.

U.S. Pat. No. 4,587,059 defines a process for the preparation of monomeric 2-cyanoacrylates comprising the steps of (a) reacting (i) a 2,4-dicyanoglutarate with (ii) formaldehyde, cyclic or linear polymers of formaldehyde, or a mixture thereof, in the presence of between about 0.5 and about 5 mols of water per mol of 2,4-dicyanoglutarate, at an acid pH of about 3 to slightly less than 7, and at a temperature of about 70 to about 140, to form an oligomeric intermediate product, and (b) removing water that is present from step (a) and thermolyzing the oligomeric intermediate product for a period of time sufficient to effect its conversion to monomeric 2-cyanoacrylates.

Commercial production of cyanoacrylate monomers ordinarily relies on the depolymerisation of a prepolymer formed under Knoevenagel condensation reaction conditions, as noted above. Still today the Knoevenagel condensation reaction is believed to remain the most efficient and prevalent commercial method for producing high yields of monofunctional cyanoacrylates. Nevertheless, it would be desirable to not have to resort to thermally induced depolymerisation of a prepolymer produced by the Knoevenagel condensation reaction. This prospect may also enable facile access to highly useful difunctional monomers, such as so-called bis-cyanaocrylates or hybrid materials of cyanoacrylate and other polymerisable or reactive functionality.

Iminium salts are salts of imines, which are in turn reaction products of carbonyl-containing compounds and amines. General methods of simple imine formation are described for instance in R. J. Vijin et al., *Synthesis*, 573 (1994) and U.S. Pat. Nos. 2,582,128 and 5,744,642.

And in International Patent Publication No. WO 03/086605 A2, task specific ionic liquids ("TSILs") are described. See also Davis, *Chem. Letts.*, 33 (9), 1072, (2004).

Absent from the published literature, however, is the use of iminium salts and/or ionic liquids in the preparation of electron deficient olefins, such as 2-cyanoacrylates. Until now.

SUMMARY OF THE INVENTION

Unlike the state of the technology, the present invention provides a direct, or substantially "crackless", synthesis of electron deficient olefins, such as 2-cyanoacrylate ester monomers, using an iminium salt. The iminium salt may be termed an "ionic liquid" (or "IL") or a task specific ionic liquid (or, "TSIL"), as will be discussed in more detail below. The synthesis hereby provided may be catalysed or uncatalysed.

In the synthesis, a novel composition of matter is used. That composition of matter embraces structure I:

where $R_1$-$R_3$ are each independently selected from H, alkenyl, and alkynyl; X is an anion, such as a non-nucleophilic and/or an acidic anion; and $R_4$ is a hydrocarbon moiety comprising a tertiary carbon which is attached to the N atom, where the tertiary carbon atom is attached to or part of one or more substituents selected from linear, branched, or cyclic alkyl or alkenyl, or one or more together form a cyclic or polycyclic (as the case may be) structure, which itself(themselves) may have substituents attached thereto.

The synthesis may likewise use an IL having a melting point less than 100° C., which in its molten form contains only ions. The IL embraces the iminium salt set forth below in structure I:

where $R_1$-$R_3$ are each independently selected from H, alkenyl, and alkynyl; X is a non-nucleophilic and/or an acidic anion; and $R_4$ is a hydrocarbon moiety comprising a tertiary carbon which is attached to the N atom, where the tertiary carbon atom is attached to or part of one or more substituents selected from linear, branched, or cyclic alkyl or alkenyl, or one or more together form a cyclic or polycyclic (as the case may be) structure, which itself(themselves) may have substituents attached thereto.

The synthesis may be defined by a process for the preparation of a reactive electron deficient olefin, steps of which comprise (a) providing:
an iminium salt within structure I:

where $R_1$-$R_3$ are each independently selected from H, alkenyl, and alkynyl; X is a non-nucleophilic and/or acidic anion; and $R_4$ is a hydrocarbon moiety comprising a tertiary carbon which is attached to the N atom, where the tertiary carbon atom is attached to or part of one or more substituents selected from linear, branched, or cyclic alkyl or alkenyl, or one or more together form a cyclic or polycyclic (as the case may be) structure, which itself(themselves) may have substituents attached thereto; and a compound containing a methylene linkage having at least one electron withdrawing substituent attached thereto, where the electron withdrawing substituent is selected from nitrite, carboxylic acids, carboxylic esters, sulphonic acids, ketones and nitro;

(b) reacting the iminium salt of structure I and the compound under appropriate conditions and for a time sufficient to yield a reactive electron deficient olefin; and (c) separating from the reaction mixture of step (b) the so formed reactive electron deficient olefin to yield the reactive electron deficient olefin.

Optionally, steps (d)-(g) may also be performed in connection with this process. In step (d), for instance, that which remains from step (b) may be treated with alkali to yield an amine used in the formation of the iminium salt within structure I, used in step (a).

Optionally, in step (e) the so formed amine may be separated from the treatment of step (d).

Optionally, in step (f) that which remains from step (e) may be treated with acid to yield protonated X, as defined in connection with structure I.

Optionally, in step (g) the so formed protonated X may be separated from the treatment of step (f).

The synthesis may be defined by a process for the preparation of a 2-cyanoacrylate ester, steps of which comprise (a) providing as reactants a mixture of formaldehyde or a source thereof and a primary amine having a nitrogen atom attached to a tertiary carbon atom to form an imine;

(b) reacting the imine with an acid under appropriate conditions and for a time sufficient to yield an iminium salt in liquid form;

(c) providing an alkyl cyanoacetate and reacting the iminium salt from step (b) therewith; and (d) separating from the mixture the so-formed 2-cyanoacrylate ester to yield 2-cyanoacrylate ester.

Optionally, steps (e)-(h) may also be performed in connection with this process. In step (e), for instance, that which remains from step (d) may be treated with alkali to yield the primary amine used in step (a).

Optionally, in step (f), the so formed amine may be separated from the treatment of step (e).

Optionally, in step (g), that which remains from step (f) may be treated with acid to yield the acid used in step (b).

Optionally in step (h) the so formed acid may be separated from the treatment of step (g).

In any of these aspects, the process may be conducted with or without added catalyst. When a catalyst is added, desirably the catalyst should be one that is not a solely basic nucleophile. Thus, an acidic system would be preferred and a ditropic system may be used, as well.

DETAILED DESCRIPTION OF THE INVENTION

As noted above, the present invention provides a synthesis, in which a novel composition of matter is used. That composition of matter embraces structure I:

where $R_1$-$R_3$ are each independently selected from H, alkenyl, or alkynyl; X is an anion, such as a non-nucleophilic and/or an acidic anion; and $R_4$ is a hydrocarbon moiety comprising a tertiary carbon which is attached to the N atom, where the tertiary carbon atom is attached to or part of one or more substituents selected from linear, branched, or cyclic alkyl or alkenyl, or one or more together form a cyclic or polycyclic (as the case may be) structure, which itself(themselves) may have substituents attached thereto. The hydrocarbon moiety comprising a tertiary carbon of $R_4$ may also be linked to one or more hydrocarbon moieties comprising a tertiary carbon, which moieties themselves may be the same or different and which may be the same or different from the hydrocarbon moiety comprising a tertiary carbon of $R_4$. The hydrocarbon moiety comprising a tertiary carbon of $R_4$ may alternatively be substituted with a heterocycle bearing a positive charge to which is associated an anion. The hydrocarbon moiety comprising a tertiary carbon of $R_4$ may still alternatively be substituted with a heteroatom or group of heteroatoms bearing a negative charge to which is associated a cation.

The synthesis may likewise use an IL having a melting point less than 100° C., which in its molten form contains only ions. The IL is also not distillable at a pressure of 1 mBar and a temperature of 100° C. The IL is in the liquid state at a temperature in the range of −10° C. to +250° C., such as in the range of 15° C. to +250° C., desirably in the range of 50° C. to +150° C. The IL embraces the iminium salt set forth below in structure I:

where $R_1$-$R_3$ are each independently selected from H, alkenyl, or alkynyl; X is an anion; and $R_4$ is hydrocarbon moiety comprising a tertiary carbon which is attached to the N atom, where the tertiary carbon atom is attached to or part of one or more substituents selected from linear, branched, or cyclic alkyl or alkenyl, or one or more together form a cyclic or polycyclic (as the case may be) structure, which itself(themselves) may have substituents attached thereto. The hydrocarbon moiety comprising a tertiary carbon of $R_4$ may also be linked to one or more hydrocarbon moieties comprising a tertiary carbon, which moieties themselves may be the same or different and which may be the same or different from the hydrocarbon moiety comprising a tertiary carbon of $R_4$. The hydrocarbon moiety comprising a tertiary carbon of $R_4$ may alternatively be substituted with a heterocycle bearing a positive charge to which is associated an anion. The hydrocarbon moiety comprising a tertiary carbon of $R_4$ may still alternatively be substituted with a heteroatom or group of heteroatoms bearing a negative charge to which is associated a cation.

In one aspect, the invention provides a synthesis defined by a process for the preparation of a reactive electron deficient olefin, steps of which comprise (a) providing:
 an iminium salt within structure I:

where $R_1$-$R_3$ are each independently selected from H, alkenyl, and alkynyl; X is an anion, such as a non-nucleophilic and/or an acidic anion; and $R_4$ is a hydrocarbon moiety comprising a tertiary carbon which is attached to the N atom, where the tertiary carbon atom is attached to or part of one or more substituents selected from linear, branched, or cyclic alkyl or alkenyl, or one or more together form a cyclic or polycyclic (as the case may be) structure, which itself(themselves) may have substituents attached thereto; and a compound containing a methylene linkage having at least one electron withdrawing substituent attached thereto, where the electron withdrawing substituent is selected from nitrile, carboxylic acids, carboxylic esters, sulphonic acids, ketones or nitro;

(b) reacting the iminium salt of structure I and the compound under appropriate conditions and for a time sufficient to yield a reactive electron deficient olefin; and (c) separating from the reaction mixture of step (b) the so formed reactive electron deficient olefin to yield the reactive electron deficient olefin.

Optionally, in step (d) that which remains from step (b) may be treated with alkali to yield an amine used in the formation of the iminium salt within structure I, used in step (a).

Optionally, in step (e) the so formed amine may be separated from the treatment of step (d).

Optionally, in step (f) that which remains from step (e) may be treated with acid to yield protonated X, as defined in connection with structure I.

Optionally, in step (g) the so formed protonated X may be separated from the treatment of step (f).

In another aspect, the invention provides a synthesis defined by a process for the preparation of a 2-cyanoacrylate ester, steps of which comprise (a) providing as reactants a mixture of formaldehyde or a source thereof and a primary amine having a nitrogen atom attached to a tertiary carbon atom to form an imine;

(b) reacting the imine with an acid under appropriate conditions and for a time sufficient to yield an iminium salt in liquid form;

(c) providing an alkyl cyanoacetate and reacting the iminium salt from step (b) therewith; and (d) separating from the mixture the so-formed 2-cyanoacrylate ester to yield 2-cyanoacrylate ester.

Optionally, in step (e) that which remains from step (d) may be treated with alkali to yield the primary amine used in step (a).

Optionally, in step (f) the so formed amine may be separated from the treatment of step (e).

Optionally, in step (g) that which remains from step (f) may be treated with acid to yield the acid used in step (b).

Optionally, in step (h) the so formed acid may be separated from the treatment of step (g).

In these processes, the hydrocarbon moiety comprising a tertiary carbon of $R_4$ may also be linked to one or more hydrocarbon moieties comprising a tertiary carbon, which moieties themselves may be the same or different and which may be the same or different from the hydrocarbon moiety comprising a tertiary carbon of $R_4$. The hydrocarbon moiety comprising a tertiary carbon of $R_4$ may alternatively be substituted with a heterocycle bearing a positive charge to which is associated an anion. The hydrocarbon moiety comprising a tertiary carbon of $R_4$ may still alternatively be substituted with a heteroatom or group of heteroatoms bearing a negative charge to which is associated a cation.

Of course, the invention also provides a process for using iminium salts to prepare reactive electron deficient olefins, such as 2-cyanoacrylate esters.

For instance, here a process for the preparation of a 2-cyanoacrylate ester is provided, steps of which comprise (a) providing as reactants a mixture of formaldehyde or a source thereof and a primary amine having a nitrogen atom attached to a tertiary carbon atom to form an imine;

(b) reacting the imine with an acid under appropriate conditions and for a time sufficient to yield an iminium salt in liquid form;

(c) providing an alkyl cyanoacetate and reacting the iminium salt from step (b) therewith; and (d) separating from the mixture the so-formed 2-cyanoacrylate ester to yield 2-cyanoacrylate ester.

Optionally, in step (e) that which remains from step (d) may be treated with alkali to yield the primary amine used in step (a).

Optionally, in step (f) the so formed amine may be separated from the treatment of step (e).

Optionally, in step (g) that which remains from step (f) may be treated with acid to yield the acid used in step (b).

Optionally, in step (h) the so formed acid may be separated from the treatment of step (g).

In any of these aspects, the process may be conducted with or without added catalyst, as noted above.

The novel iminium salts are useful in the preparation of electron deficient olefins, and if desired the amine and/or acid used in the process may be recovered and/or recycled. The novel iminium salts have substantially zero vapour pressure as noted above and are not distillable at a pressure of 1 mBar and a temperature of 100° C., whereas the electron deficient olefins are volatile and may be isolated by direct vacuum distillation from the reaction vessel that contains quaternary ammonium salts as byproducts from the reaction which formed the electron deficient olefin. Further, the original amine used to form the iminium salt may be recovered and recycled by treatment of the quaternary ammonium salt that forms during the formation of the electron deficient olefin, by base workup, for example by aqueous sodium hydroxide. Still further, the acid used in salt formation (e.g., benzene sulfonic acid) may also be recovered by subsequent acidification using an acid (e.g., aqueous HCl) with a $pK_a$ lower than that of the original acid used in forming the iminium salt.

Reference to the figures may be useful to appreciate further the present invention, which is described in more detail below and in the Example section that follows below.

Thus, as an initial reactant, either in the inventive processes or to form the iminium salt and/or ionic liquid useful therewith, are aldehyde compounds having the structure R—CH=O, where R is hydrogen, vinyl or propargyl. The aldehyde compound may be an aldehyde itself or a source of an aldehyde, such as one that yields an aldehyde like formaldehyde under appropriate reaction conditions. The aldehyde compound in a desirable embodiment includes formaldehyde (or a source thereof, such as paraformaldehyde, formalin, or 1,3,5-trioxane) or vinyl aldehydes, such as acrolein.

Figure 1:
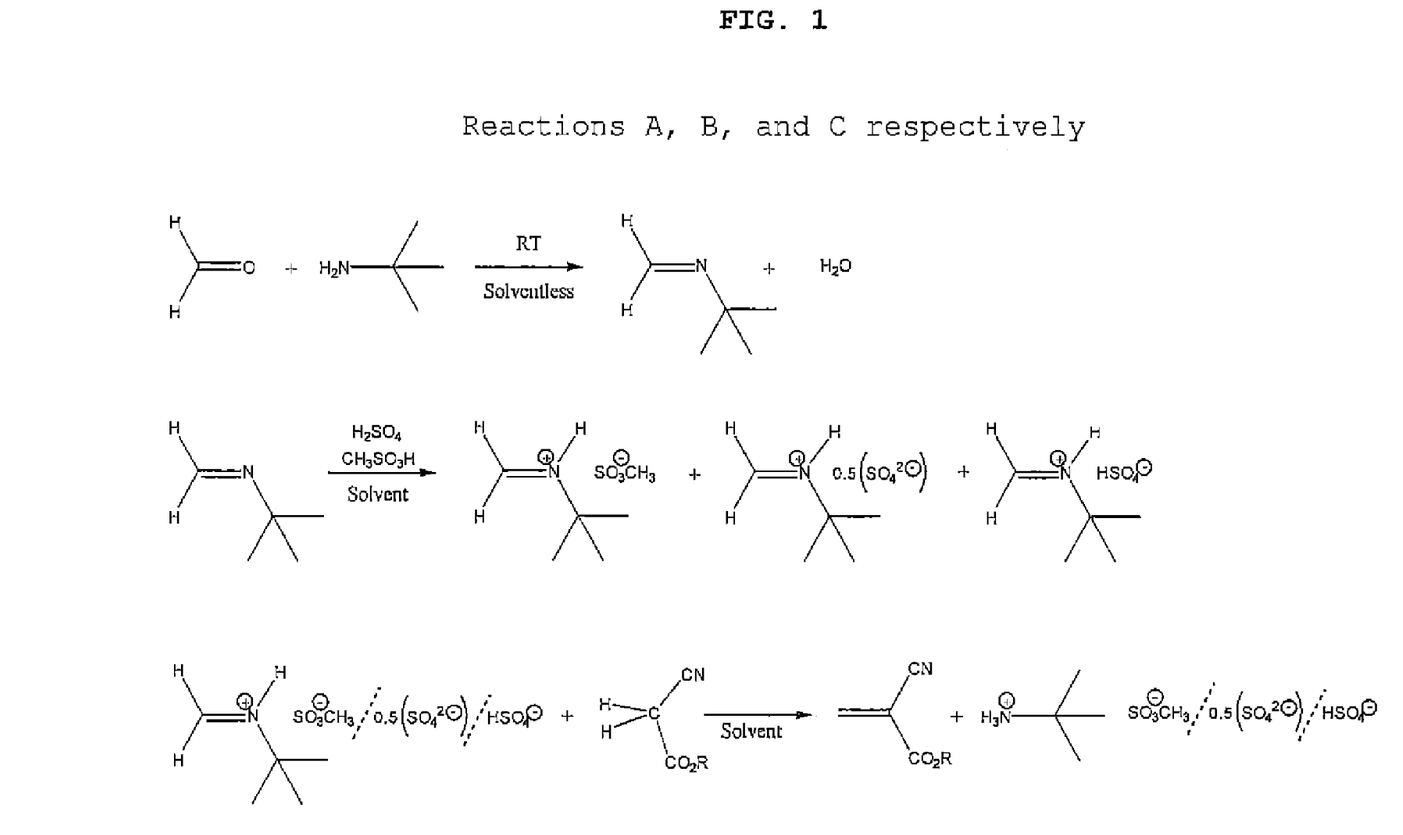
FIG. 1 depicts a synthetic scheme by which 2-cyanoacrylate esters may be prepared from an iminium salt (shown in the third step), which itself is prepared in the preceding two steps according to the present invention.

As a reactant with such an aldehyde is a primary amine. Sterically hindered primary amines are particularly desirable, such as t-alkyl primary amines. In FIG. 1, t-butylamine is shown. Rohm and Haas Co., Philadelphia, Pa. has sold commercially for a number of years a series of sterically hindered primary amines, which are designated as PRIMENE-brand amines.

Figure 2:
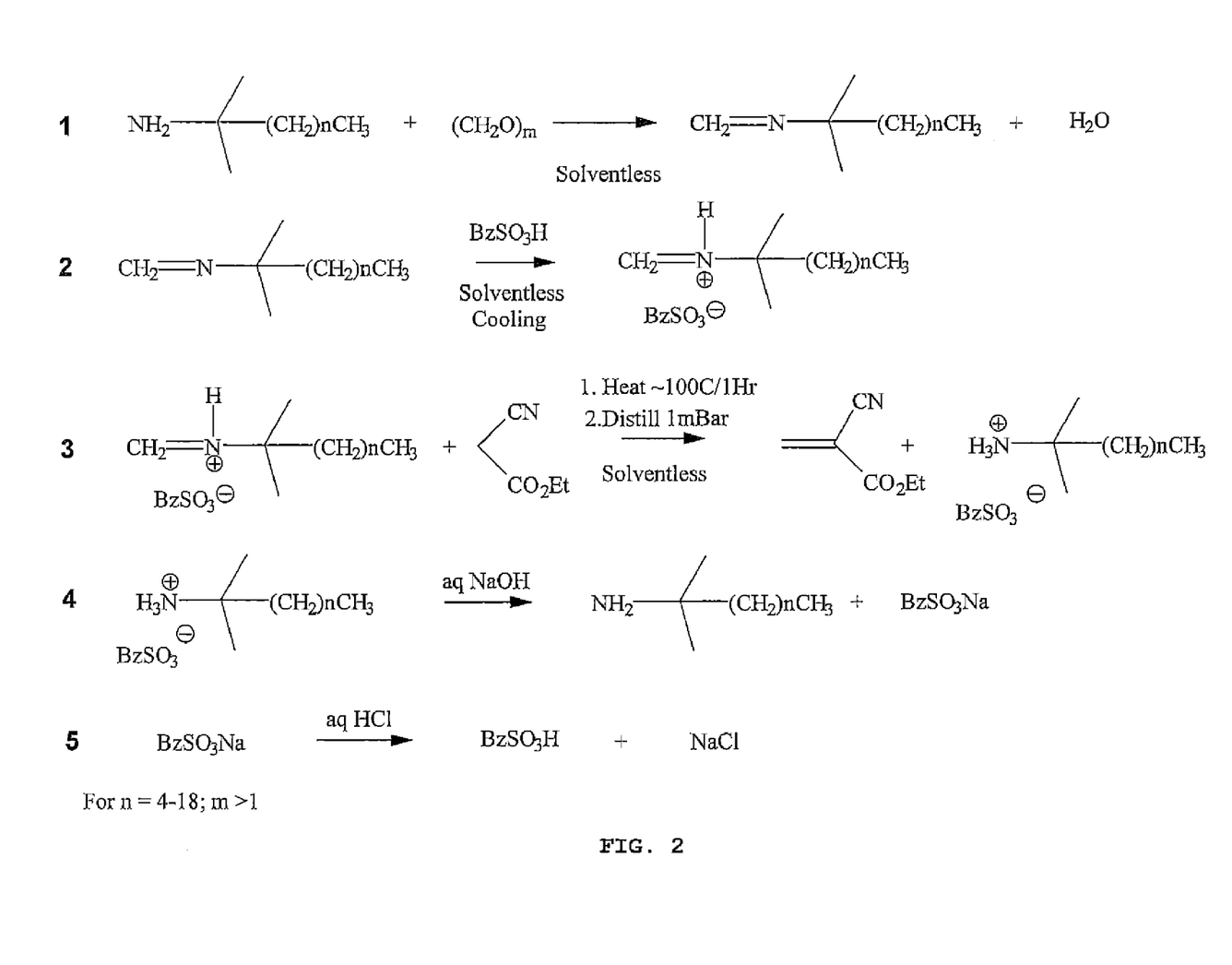
FIG. 2 depicts synthetic schemes according to the present invention by which 2-cyanoacrylate esters may be prepared from an iminium salt, and where not only may the original amine from which the imine was prepared be recovered and/or recycled, but also the acid used to form the iminium salt may be recovered and/or recycled.

For instance, with reference to FIG. 2, t-alkyl primary amines are shown, illustrative of which are PRIMENE 81-R and PRIMENE JM-T. These PRIMENE-brand t-alkyl primary aliphatic amines have highly branched alkyl chains in which the amino nitrogen atom is linked to a tertiary carbon. These primary amines consist of mixtures of isomeric amines, with PRIMENE 81-R consisting of an isomeric mixture with $C_{12}$-$C_{14}$ carbon branches and having an average molecular weight of 185 and PRIMENE JM-T consisting of an isomeric mixture with $C_{16}$-$C_{22}$ carbon branches and having average molecular weight of 269.

PRIMENE MD, also known as menthanediamine (1,8-diamino-p-menthane) or (4-amino-α,α, 4-trimethyl-cyclohexanemethanamine, CAS No. 80-52-4), is a primary alicyclic diamine, in which both amino groups are attached to tertiary carbon atoms. PRIMENE MD is shown below as structure III. Like other t-alkyl primary amines, such as t-octylamine ("TOA"), menthanediamine is somewhat less reactive than similar straight chain diamines. PRIMENE TOA has tertiary octyl chains and a molecular weight of 129.

PRIMENE RB3 is an additional example of a commercially available primary amine. A version of a diiminium salt derived from PRIMENE MD after condensation with paraformaldehyde and subsequent acidification is shown below in structure IV.

Examples of anion X in structure IV include but are not limited to $PF_6$, $BF_4$, $CH_3SO_3$, and benzene sulfonate.

Imines, e.g., formed by reaction of the primary amine with the aldehyde, may be converted into iminium salts by contacting them with an acidic species, such as trifluoroacetic acid, acetic acid, sulphuric acid, methane sulfonic acid, benzene sulfonic acid and camphor sulfonic acid (see e.g. J. March at 802, and references cited therein; see also M. B. Smith, Organic Synthesis, McGraw Hill International, Chemistry Series, 1302 (1994) and references cited therein and Abbaspour Tehrani and De Kimpe, Science of Synthesis, 27, 313 (2004), and references cited therein). (See also FIG. 1, B).

Some iminium salts are available commercially, such as Eschenmoser's salt from Aldrich Chemical Co. Eschenmoser's salt has been used in the synthesis of conventional acrylates, see e.g. B. Hin et al., *J. Org. Chem.*, 67, 7365 (2002). This iminium salt has also been used in Mannich reactions [Holy et al., *Tetrahedron*, 35, 613 (1979), and Bryson et al., *J. Org. Chem.*, 45, 524 (1980)].

Indeed, imines and iminium salts may even be formed without the use of a carbonyl compound at the outset. Thus, for example, Jahn and Schroth have described a method for the preparation of iminium salts, *Tett. Lett.*, 34 (37), 5863 (1993), in which alpha-chloroethers may be used to form "Mannich reagents", which are iminium salts. Oxidation of amines can lead to imines, as well, and hence iminium salts.

As noted above, the present invention relates to novel iminium salts embraced by structure I where each of the substituents are as defined above.

More specific examples of iminium salts within structure I include those where each of $R_1$, $R_2$ and $R_3$ are H, alkenyl or alkynyl, such as vinyl or propargyl, and $R_4$ is a branched hydrocarbon moiety that attaches the charged nitrogen atom of structure I, to an organic cation, such as those known to those skilled in the art such as quaternary ammonium, imidazolium, and phosphonium (see e.g. International Patent Publication No. WO 03/086605A2), and X is a non-nucleophilic and/or acidic anion, such as $PF_6$, $BF_4$, $AsF_6$, $SbF_6$, $Tf_2N$, $(CN)_2N$, triflate, camphorsulfonate, benzenesulfonate, saccharinate, acesulfamate, or $MF_6$ where M is Nb or Ta, or nitrate, $CF_3CO_2$, halide, phosphate, perchlorate or $CH_3SO_3$, the latter of which may be the same or different to the anion counterbalancing charge for the organic cation. See also Davis et al. in *Ionic Liquids in Synthesis*, P. Wasserscheid and T. Welton, eds., Wiley-VCH Verlag GmbH & Co. KGaA, Chapter 2 (2002).

The so-formed iminium salts are then reacted with compounds containing a methylene linkage having at least one electron withdrawing substituent attached thereto. In these compounds, the electron withdrawing substituent is selected from nitrile, carboxylic acids, carboxylic esters, sulphonic acids, ketones or nitro. In a desirable embodiment, these compounds have two or more electron withdrawing substituents, which may be the same or different, such as nitrile and carboxylic acid ester—in this case, a cyanoacrylate. (See FIG. 1, C).

Representative examples of these compounds include malononitrile, malonic acid and its esters, ethyl nitroacetate, cyanoacetic acid and its esters, 4-cyclopentene-1,3-dione, cyclopentane-1,3-dione, 4-cyclohexene-1,3-dione, cyclohexane-1,3-dione, 2,2-dimethyl-1,3-dioxane-4,6-dione (Meldrum's acid), and tetronic acid, some of which are commercially available for instance from The Aldrich Chemical Co. A particularly desirable example is the ethyl ester of cyanoacetic acid.

The structures below illustrate the olefinic products that would result from a reaction involving iminium salts with paraformaldehyde, using the above reactants.

II

Here, when a source of formaldehyde is used, n is 0 in structure II and a methylenic compound results with X and Y being nitrile, carboxylic acid, carboxylic acid esters; X being nitro and Y being carboxylic acid ester; or X being nitrile and Y being carboxylic acid ester, the latter combination giving rise to 2-cyanoacrylates using alkyl cyanoacetates as a substrate, for example. When acrolein is used, n is 1 and the same combinations of X and Y can apply in structure II.

The electron deficient olefin so formed by the inventive processes may be a variety of olefins having at least one electron withdrawing group attached thereto. In a desirable embodiment, as noted above with respect to the second reactant, the electron deficient olefin so formed will have two or more electron withdrawing groups attached thereto, which may be the same or different. Particularly desirable products have two electron withdrawing groups attached thereto which are different, such as 2-cyanoacrylate esters.

Representative examples of 2-cyanoacrylate esters so formed by the inventive processes include methyl, ethyl, n-propyl, i-propyl, propargyl, n-butyl, i-butyl, n-pentyl, n-hexyl, 2-ethylhexyl, n-octyl, n-nonyl, oxononyl, n-decyl, n-dodecyl, allyl, ethynyl, 2-butenyl, cyclohexyl, phenyl, phenethyl, tetrahydrofurfuryl, chloroethyl, 2,2,2-trifluoroethyl, hexafluoroisopropyl, methoxymethyl, methoxyethyl, methoxybutyl, ethoxyethyl, propoxyethyl, butoxymethyl, butoxyethyl and dimethyl siloxane esters of 2-cyanoacrylic acid.

The electron deficient olefin may also be a compound having one end terminating with a cyanoacrylate, cyanopentadienoate, or alkylene derived from dimalonate or malononitrile and another end terminating with a group selected from branched and unbranched alkyl esters, esters containing aromatics and heterocylic nuclei, acrylates, cyanoacrylates, siloxanes, blocked and unblocked isocyanates, anhydrides, silanes, vinyls, and acetylenes. Of course, salt is also formed. (See FIG. 1, C). The salt, or salt mixtures, may be in the liquid state at the reaction temperature.

The reaction of the inventive process may proceed with or without heating or cooling, depending of course on the specific reactants and the scale of the reaction. Decomposition of the source of formaldehyde, e.g., paraformaldehyde, may occur under gentle heating up to a temperature of 70° C., to liberate formaldehyde in situ in the reaction medium. The temperature may be reached through an external heating element or internally by means of the exotherm that may be generated depending on the identity of the reactants. The temperature of the reaction should be controlled however to accommodate any such exothermic processes.

The time of reaction may be monitored by reference to the formation of the desired electron deficient olefin product. A $^1H$ NMR spectrometer is a particularly useful tool in this regard. The time of reaction may be as little as 30 minutes, for instance, or longer or shorter for that matter depending again on the identity of the specific reactants, the scale of the reaction and whether heat is added to the reaction conditions.

Once formed, the electron deficient olefin product may be isolated by direct distillation under vacuum out of the reaction mixture or by freezing it in a solid form and separating off the liquid phase. The former method is particularly useful in the case of 2-cyanoacrylates (particularly their lower esters) which may be relatively volatile.

The electron deficient olefin so formed by the inventive processes may be stabilized during the synthesis and/or isolation procedure, and also in the isolated product to improve its shelf life. Suitable stabilizers include free radical stabilizers and acidic stabilizers. For example, free radical stabilizers include hydroquinone, pyrocatechol, resorcinol or derivatives thereof, such as hydroquinone monoethyl ether, or phenols, such as di-t-butylphenol or 2,6-di-t-butyl-p-cresol, 2,2'-methylene-bis-(4-methyl-6-t-butylphenol), bisphenol A, dihydroxydiphenylmethane, and styrenized phenols.

For example, acidic stabilizers include sulfuric acid, hydrochloric acid, sulfonic acids, such as methane, ethane or higher sulfonic acids, p-toluene sulfonic acid, phosphoric acid or polyphosphoric acids, silyl esters of strong acids, such as trialkyl chlorosilanes, dialkyl dichlorosilanes, alkyl trichlorosilanes, tetrachlorosilane, trialkyl silylsulfonic acids, trialkyl silyl-p-toluene sulfonates, bis-trialkyl silylsulfate and trialkyl silylphosphoric acid esters.

The amount of either stabilizer used to stabilize the electron deficient olefin prepared by the inventive processes is well known to those of ordinary skill in the art, and may be varied depending on the properties of the resulting composition made from the so formed electron deficient olefin.

The following examples are intended to illustrate but in no way limit the present invention.

EXAMPLES

Example 1

PRIMENE Imines (FIG. 2, Step 1)

PRIMENEs TOA, 81-R and JM-T were used to prepare imines by reaction of the amines with stoichiometric equivalents of paraformaldehyde and removal of water of condensation. All imines formed were distillable liquids and existed in stable monomeric imine forms as confirmed by $^1$H NMR 60 MHz (CDCl$_3$) 2H D 7.16, 7.09 ppm (TOA imine); 2H s (br) 7.45 ppm (81-R imine) and (CD$_3$COCD$_3$) 2H 6.86 PPM (JM-T Imine) and FTIR (1650 cm$^{-1}$ for each).

PRIMENE Iminium Salts (FIG. 2, Step 2)

Distilled imines were analysed by Karl-Fischer titration and shown to be essentially free from water (<20 ppm). These imines were treated with a stoichiometric equivalent of acid while cooling. Iminium salts were prepared from the following acids: methane sulfonic acid, benzene sulfonic acid, sulphuric acid and mixtures of some of these.

PRIMENE TOA iminium methane sulfonate forms a viscous liquid that begins to show signs of crystallisation at room temperature after standing for several weeks. PRIMENE 81-R iminium methane sulfonate forms a clear low viscosity IL at room temperature and is stable in liquid form. This material remains liquid on cold storage (4° C.) for prolonged periods (weeks). PRIMENE JM-T iminium methane sulfonate behaves similarly to PRIMENE 81-R iminium salts. Benzene sulfonate iminium salts also were formed as liquids, even though the starting acid is a solid.

The FTIR spectra of the iminium salts shows loss of the imine signal (1650 cm$^{-1}$) and the iminium protons are poorly resolved and broadened in the 60 MHz $^1$H NMR spectra.

Importantly, the water-white or pale yellow, clear, low viscosity liquid were not distillable at a pressure of 1 mbar and a temperature of 100° C.

Synthesis of Electron Deficient Olefins (FIG. 2, Step 3)

Ethyl cyanoacetate was added directly to a PRIMENE iminium methane sulfonate (or benzene sulfonate) at a 20 mmol level and a ratio of 1:1.1. The low viscosity mixture was heated at a temperature at 100° C. for a period of time between about 30 minutes and 1 hour and stirred with a conventional magnetic stirring bar. After heating, ethyl-2-cyanoacrylate monomer was distilled directly from the reaction vessel and characterised by $^1$H NMR. The yield and purity of the monomer after first distillation (i.e, directly from the reaction vessel) varied according to anion of the iminium salt. Yields and purity of bulk isolated cyanoacrylate monomer evaluated by $^1$H NMR against ethyl cyanoacetate starting material were: 64%, 90% pure (methane sulfonate anion); 64%, 80% pure (benzene sulfonate anion); 46%, 77% pure (mixture 1:1 methane sulfonate/sulfuric acid anions). The t-butyl and octyl cyanoacrylate esters were also made in a similar fashion with similar yields and purities.

When malononitrile was used in place of ethyl cyanoacetate, the dinitrile alkylidene was isolated after only a 20 minute reaction time at a temperature of 70° C. in a yield of 61% and initial purity of 80% after a first distillation from the reaction vessel.

When dimethyl malonate was used in place of ethyl cyanoacetate, the alkylidene dimethylmalonate was isolated after 1 hour at a temperature of 100° C. in a 30% yield.

Recovery of PRIMENE Amine (FIG. 2, Step 4)

After direct distillation of reactive electron deficient olefin from the reaction vessel, the residue was treated with 25 mmol of sodium hydroxide in 100 mls water and extracted with dichloromethane to produce almost 100% recovery of the starting PRIMENE amine. The $^1$H NMR spectra of recovered PRIMENE TOA and PRIMENE 81-R, for instance, were virtually identical to the starting material PRIMENE reagents.

Recovery of Organic Acids (FIG. 2, Step 5

Aqueous sodium benzene sulfonate resulting from the previous step is acidified to pH 1 with hydrochloric acid and is extracted with dichloromethane to recover benzene sulfonic acid.

Example 2

In this example, a variety of imines were synthesized and characterized using the flowing instrumentation:

NMR spectra were recorded with a JNM-MY60 (60 MHz for 1H), or a Varian UNITY-300 (300 MHz for $^1$H and 75.5 MHz for $^{13}$C NMR). Chemical shifts δ are given in ppm relative to residual peaks of deuterated solvents, and coupling constants J are given in Hertz.

IR spectra were recorded on a Nicolet 380 FT-IR spectrometer and measured as KBr pellets or as oils between KBr plates.

GC/MS spectra were obtained on a PE-GCMS Clarus 500, Perkin Elmer GCMS spectrometer.

All amines (PRIMENE TOA, 81-R, JMT, MD from Rohm and Haas), acids (methane sulfonic, acetic, p-toluene sulfonic, benzene sulfonic, sulfuric, and phosphoric from Aldrich), solvents (toluene, benzene, ether, heptanes, hexanes, dichloromethane, chloroform from Aldrich), n-butyl lactoyl cyanoacetate (from Degussa), other chemicals (cyanoacetic acid, ethyl cyanoacetate, 2-hydroxylethyl acrylate, 2-hydroxyethyl methacrylate, hydroxypropyl acrylate, hydroxypropyl methacrylate from Aldrich) were used as purchased without further purification.

The corresponding imines of PRIMENEs were produced with paraformaldehyde or formaldehyde according to the procedure in U.S. Pat. No. 2,582,128. Usually, acetates were synthesized with cyanoacetic acid and corresponding alcohol by standard Dean-Stark procedure through removal of water (for bi-functional acrylate acetates, hydroquione was introduced as a stabilizer). Silicon-based acetates were prepared according to the procedure set forth in European Patent Publication No. 0 459 617 A1 (Mikuni et al.).

Synthesis of N-Methyldidene-t-Butylamine

The imine was prepared using a modified procedure of R. J. Vijin, et al., *Synthesis*, 573-578 (1994); U.S. Pat. No. 2,582, 128.

t-Butylamine (146 g, 2 mol) was added portionwise with stirring over a period of time of 30 minutes to paraformaldehyde (60 g), while cooling to maintain the reaction temperature near room temperature. The resulting mixture was stirred for a period of time of 30 minutes at room temperature, after which time the organic layer was separated and dried over anhydrous sodium sulfate. A slight yellow filtrate was collected is a mixture of monomer and trimer. The filtrate was then distilled through a short packed column at a rate such that the temperature of the vapour did not rise above 65° C. The pot temperature varied between 110° C. and 120° C. N-Methyldidene-t-butylamine (Bp 64-65° C.) was collected in a 70% yield as a colourless oil. The pure monomer was observed to be not stable, and partly transformed into trimer in several seconds. FT-IR spectra showed the absorption of C=N (monomer, 1596.4 cm$^{-1}$) significantly decreases in several seconds. NMR spectra showed it is mixture of trimer and monomer. $^1$H NMR (60 MHz, CDCl$_3$): δ 7.29 (s, 2 H, monomer), 3.51 (s, 6 H, trimer), 1.18 (s, 9 H, monomer), 1.11 (s, 27 H, trimer). Monomer/trimer=3.5:1; FT-IR (film): mixture of monomer and trimer, 3027.7, 2970.3, 2912.1, 2797.1, 1601.1 (monomer, C=N), 1477.8, 1392.0, 1268.9, 1175.6, 1150.7, 1025.6, 909.7, 898.0 cm$^{-1}$; GC/MS (EI), m/z (%): 85 (10) [M$^+$], 70 (100), 57 (30), 41 (70).

Synthesis of N-Methyldidene Trioctyl Imine

To N-methyldidene trioctyl amine (70 g, 0.54 mol) in a 250 mL flask was added portionwise paraldehyde (17.1 g, 0.57 mol) at ice water, cooling bath temperature. After the addition was complete, the mixture was allowed to stir for a period of time of 30 minutes at room temperature. The mixture was dried over anhydrous sodium sulfate and purified by distillation (92-100° C.) in a 87% yield.
$^1$H NMR (60 MHz, CDCl$_3$): δ 6.95 (s, 2 H), 1.29 (s, 2 H), 0.87 (s, 6 H), 0.62 (s, 9 H); FT-IR (film): 2952.5, 2904.9, 1650.9, 1470.3, 1381.1, 1362.8, 1240.4, 1140.3, 1024.2, 914.7 cm$^{-1}$; GC/MS (EI), m/z (%): 142 (5) [M$^+$+H], 126 (80), 113 (10), 97 (10), 84 (20), 70 (100), 57 (95), 41 (60).

Synthesis of PRIMENE 81-R Imine

PRIMENE 81-R amine (450 g, 2.43 mol) and paraformaldehyde (76.6 g, 2.55 mol) were mixed with stirring for a period of time of 16 hours at room temperature. To the mixture was added anhydrous sodium sulfate, which was filtered away. Excess paraformadlehye was removed and collected through a water-cooled condenser at a temperature of 70° C. and a pressure of 1-10 bar. The mixture was purified by vacuum distillation through a splash head to yield a colourless oil (100-110° C./0.2 mbar) $^1$H NMR (60 MHz, d6-Acetone): δ 7.21 (br, s, 2 H), 0.83-1.19 (m, 28 H); FT-IR (film): 2959.1, 2873.3, 1650.9, 1463.5, 1378.1, 1024.3, 914.7 cm$^{-1}$.

Synthesis of PRIMENE JMT Imine

PRIMENE JMT amine (131.2 g, 0.49 mol) and paraformaldehyde (15.3 g, 0.51 mol) were mixed with stirring at room temperature. To the mixture was added anhydrous sodium sulfate, which was filtered away. The yellow mixture was purified by vacuum distillation to yield about 100 g of a colourless oil (120-125° C./1 mbar). $^1$H NMR (60 MHz, CDCl$_3$): δ 7.30 (s, 2 H), 1.95-0.87 (m, >33 H); FT-IR (film): 2957.1, 1650.6, 1463.8, 1378.1, 1147.9, 1057.7, 1023.7, 1001.5, 965.4, 915.6 cm$^{-1}$.

Synthesis of PRIMENE MD Diimine

A mixture of 1,8-diamino-p-methane (70% tech. 16.9 g) and aqueous solution of formaldehyde (37%, 17.8 g) was stirred for half of hour at room temperature. The water was then removed by the addition of pellets of potassium hydroxide and the dried organic material was distilled at 80-81° C./1 mbar, 10 g of colourless oil. $^1$H NMR (60 MHz, CDCl$_3$): δ 7.43 (s, 2 H), 7.31 (s, 2 H), 1.95-1.06 (m, 18 H); FT-IR (film): 2934.6, 2868.8, 1650.4, 1444.7, 1378.4, 1362.3, 1175.8, 1026.0 cm$^{-1}$; GC/MS (EI), m/z (%): main component (80%), 179 (20) [M$^+$-CH$_3$], 166 (18), 152 (40), 138 9300, 124 (20), 109 (17), 95 (40), 81 (50), 70 (100), 55 (50), 41 (60).

Example 3

In this example, a variety of iminium salts were synthesized from the imines prepared above.

Synthesis of PRIMENE 81-R Iminium-MSA

Methane sulfonic acid (96 g, 1.0 mol) was added dropwise with stirring to freshly distilled PRIMENE 81-R imine (197 g, ~1.0 mol) at ice water bath temperature, and then left to warm to room temperature. The pale yellow iminium salt that formed was kept for further reaction.

Synthesis of Other Iminium Salts

Following the same procedure, the following iminium salts were prepared:

TABLE 1

|  | H$_2$SO$_4$ | H$_3$PO$_4$ | MSA | BSA | NSA | LAS |
| --- | --- | --- | --- | --- | --- | --- |
| t-Bu Imine | s | s | s | s | s | ✓ |
| PRIMENE TOA Imine | s | s | s | s | s | ✓ |
| PRIMENE 81-R Imine | ✓ | ✓ | ✓ | ✓ | ✓ | ✓ |
| PRIMENE JMT Imine | ✓ | ✓ | ✓ | ✓ | ✓ | ✓ |
| PRIMENE MD Diimine* | s | s | ✓ | ✓ | s | ✓ |

Notes:
MSA = Methanesulfonic acid; BSA = Benzenesulfonic acid; LAS = Dodecylbenzene sulfonic acid, NSA = 2-Naphthalenesulfonic acid; s = solid; ✓ = ionic liquid.
*Two mole equiv. of acid was used.

Ethyl cyanoacrylate, and other electron deficient olefins, were synthesized from a variety of iminium salts using the following general conditions. Ethyl cyanoacetate (1.0 equiv.) and iminium salt (1.0 equiv.) were mixed together with stirring under heating at a temperature of 100° C. for a period of time of 1 minute, after which vacuum distillation (0.1-1.0 mbar) at hot oil bath temperatures yielded the ethyl cyanoacrylate. In Table 2 below specific iminium salts, together with cyanoacrylate purity and yield are shown.

TABLE 2

| Iminium Salts[a] | Purity[b] (%) | Yield[c] (%) |
| --- | --- | --- |
| PRIMENE 81-R MSA | 95 | 73 |
| PRIMENE 81-R H$_2$SO$_4$ | <20 | 10 |
| PRIMENE 81-R MSA/H$_2$SO4 (1:1) | 77 | 46 |
| PRIMENE 81-R MSA/H$_2$SO$_4$ (1:4) | 70 | 21 |
| PRIMENE 81-R BSA | 79 | 64 |
| PRIMENE 81-R NSA | 0 | 0 |
| PRIMENE 81-R LAS | 79 | 50 |
| PRIMENE 81-R PTSA | 36 | 16 |
| tBu MS[d] | ~80 | ~70 |
| PRIMENE TOA MSA | 82 | 44 |
| PRIMENE MD MSA | 52 | 23 |
| PRIMENE JM-T MSA | 40 | 26 |

[a]MSA = Methanesulfonic acid, BSA = Benzenesulfonic acid, LAS = Dodecylbenzene sulfonic acid, NSA = 2-Naphthalenesulfonic acid (70%), PTSA = p-Toluenesulfonic acid monohydrate;
[b]Purity was calculated on the basis of $^1$H NMR analysis of unreactive acetate and yielded ECA;
[c]Yields based on calculated pure ECA monomer;
[d]The reaction was carried out in CDCl$_3$ solution, ECA was not isolated and the yield and purity are based on $^1$H NMR analysis.

Example 4

In this example, the following two 2-alkyl substituted cyanoacetates were obtained by direct esterification of cyanoacetic acid with a variety of alcohols in a 1:1 molar ratio in the presence of two/three drops of 2% concentrated sulphuric acid as a catalyst and toluene as solvent, to allow for the azeotropic removal of the reaction water.

Example 5

In this example, the following three alkenyl- and alkynyl-2-cyanoacetates were obtained by direct esterification of cyanoacetic acid with a variety of alcohols in the molar ratio 1.0:1.4 in the presence of 2% concentrated sulphuric acid as a catalyst and toluene as solvent, to allow for azeotropic removal of the reaction water. See D. L. Kotzev, P. C. Novakov, V. S. Kabaivanov, *die Anqewandte Makromolecular Chemie*, 92, 41-52 (1980).

Example 6

In this example, three silicon-containing 2-cyanoacetates were prepared according to European Patent Application No. EP 0 459 617.

Trimethylsilylmethyl 2-cyanoacetate

$^1$H NMR (60 MHz, CDCl$_3$): δ 3.97 (s, 2 H), 3.49 (s, 2 H), 0.20 (s, 9 H); GC/MS (EI), m/z (%): 157/156 (2/10) [M$^+$-CH$_2$], 113 (20), 84 (40), 73 (100).

Trimethylsilylethyl 2-cyanoacetate $^1$H NMR (60 MHz, CDCl$_3$): δ 4.36 (t, J=7.2 Hz, 2 H), 3.47 (s, 2 H), 1.13 (t, J=7.2 Hz, 2 H), 0.15 (s, 9H); GC/MS (EI), m/z (%): 170 (2) [M$^+$-CH$_2$], 98 (80), 73 (100).

Trimethylsilylpropyl 2-cyanoacetate $^1$H NMR (60 MHz, CDCl$_3$): δ 4.20 (t, J=7.2 Hz, 2 H), 3.50 (s, 2 H), 2.0-1.5 (m, 2 H), 0.84-0.45 (m, 2 H), 0.09 (s, 9 H); GC/MS (EI), m/z (%): 198 (2) [M$^+$-H], 113 (40), 98 (90), 73 (100).

Example 7

In this example, ethyl cyanoacrylate was prepared and the iminium salt recovered as the amine as follows.

A mixture of PRIMENE 81-R iminium-MSA (95.8 g, 0.326 mol) and cyanoacetate (36.8 g, 0.326 mol) was heated with stirring for a period of time of 1 minute at a temperature of 100° C., after which time the reaction was vacuum distilled (0.2 mbar, oil bath temperature up to 200° C.). ECA was collected as a colourless oil (33.0 g, 0.264 mol) in a yield of 73%. $^1$H NMR (60 MHz, CDCl$_3$): δ 6.92 (s, 1 H), 6.49 (s, 1 H), 4.17 (q, J=7.2 Hz, 2 H), 1.30 (t, J=7.2 Hz, 3 H); Purity (96%) checked by GC.

PRIMENE 81-R ammonium MSA salt is the main byproduct left after vacuum distillation. PRIMENE 81-R amine was recovered by adding with stirring 1 equiv. of aqueous NaOH, followed by extraction with CHCl$_3$. The organic solution was dried over sodium sulfate, and volatile solvent was removed by rotary evaporator. The residue oil (49 g) was subjected to vacuum distillation, and 36.8 g of PRIMENE 81-R amine was recovered.

Example 8

To a stirred mixture of PRIMENE 81-R iminium-MSA (5.86 g, 20 mmol) and n-butyl cyanoacetate (2.82 q, 20 mmol), was added 10 mg of hydroquione and degassed for 5 minutes at room temperature. Vacuum distillation at prewarm oil bath (0.2 mbar, oil bath temperature up to 200° C.) was then conducted to afford a colourless oil (94% purity by GC, 79% yield). $^1$H NMR (60 MHz, CDCl$_3$): δ 7.00 (s, 1 H), 6.57 (s, 1 H), 4.26 (t, J=6.0 Hz, 2 H), 0.95-1.58 (m, 7 H);

FT-IR (film): 3126.7, 2963.0, 2937.0, 2875.8, 2237.8, 1739.3, 1616.1, 1465.9, 1321.4, 1288.8, 1189.6, 989.1, 804.4 cm$^{-1}$.

Example 9

To a stirred mixture of PRIMENE 81-R iminium-MSA (5.86 q, 20 mmol) and 2-octyl cyanoacetate (3.94 g, 20 mmol), was added 10 mg of hydroquione and degassed for 5 minutes at room temperature. Vacuum distillation at pre-warm oil bath (0.2 mbar, oil bath temperature up to 200° C.) was then conducted to afford a colourless oil (Bp: 100-106° C./0.2 mbar, 95% purity, 79% yield). $^1$H NMR (60 MHz, CDCl$_3$): δ 6.97 (s, 1 H), 6.54 (s, 1 H), 5.16-4.86 (m, 1 H), 0.86-1.73 (m, 16 H); FT-IR (film): 3125.4, 2931.2, 2859.3, 2237.7, 1732.0, 1616.6, 1465.0, 1385.8, 1317.5, 1288.1, 1194.5, 1120.1, 804.4 cm$^{-1}$.

Example 10

To a stirred mixture of PRIMENE 81-R iminium-MSA (2.93 g, 10 mmol) and n-butyl lactoyl cyanoacetate (2.13 g, 10 mmol), was added 5 mg of hydroquione and degassed for 5 minutes at room temperature. Vacuum distillation at pre-warm oil bath (0.2 mbar, oil bath temperature up to 200° C.) was then conducted to afford a colourless oil (Bp: 130-140° C./0.2 mbar, 75% purity by GC, 41% yield). $^1$H NMR (60 MHz, CDCl3): δ 7.06 (s, 1 H), 6.65 (s, 1 H), 5.51-5.17 (m, 1 H), 4.26-4.06 (m, 2 H), 1.65-0.93 (m, 10 H); FT-IR (film): 3126.6, 2962.3, 2875.5, 2239.3, 1742.8, 1693.7, 1459.1, 1389.9, 1282.4, 1186.4, 1096.5, 802.8 cm$^{-1}$.

Example 11

A mixture of PRIMENE 81-R iminium-LAS (prepared by the same procedure as PRIMENE 81-R iminium-MSA with 1:1 mole equivalent of PRIMENE 81-R imine and LAS, 5.23 g, 10 mmol) and trimethylsilylmethyl 2-cyanoacetate (1.71 g, 10 mmol), was heated with stirring for a period of time of 1 minute at a temperature of 100° C., after which time vacuum distillation (0.2 mbar, oil bath temperature up to 150° C.) was performed thereon. The distillate was collected as a colourless oil (65% purity by NMR, 43% yield). $^1$H NMR (60 MHz, CDCl$_3$): δ 7.03 (s, 1 H), 6.60 (s, 1 H), 4.15 (s, 2 H), 0.11 (s, 9 H).

Example 12

A mixture of PRIMENE 81-R iminium-LAS (5.23 g, 10 mmol) and trimethylsilylethyl 2-cyanoacetate (1.85 g, 10 mmol), was heated with stirring for a period of time of 1 minute at a temperature of 100° C., after which time vacuum distillation (0.2 mbar, oil bath temperature up to 185° C.) was performed thereon. The distillate was collected as a colourless oil (61% purity by NMR, 28% yield). $^1$H NMR (60 MHz, CDCl$_3$): δ 7.09 (s, 1 H), 6.66 (s, 1 H), 4.47 (t, J=9 Hz, 2 H), 1.20 (t, J=9 Hz, 2 H), 0.11 (s, 9 H).

Example 13

A mixture of PRIMENE 81-R iminium-LAS (5.23 g, 10 mmol) and trimethylsilylpropyl 2-cyanoacetate (1.99 g, 10 mmol), was heated with stirring for a period of time of 1 minute at a temperature of 100° C., after which time vacuum distillation (0.2 mbar, oil bath temperature up to 200° C.) was performed thereon. The distillate was collected as a colourless oil (74% purity by NMR, 25% yield). $^1$H NMR (60 MHz, CDCl$_3$): δ 7.09 (s, 1 H), 6.66 (s, 1 H), 4.30 (t, J=9 Hz, 2 H), 0.75-1.78 (s, 4 H), 0.11 (s, 9 H).

Example 14

To a stirring mixture of PRIMENE 81-R iminium-MSA (5.86 g, 20 mmol) and allyl 2-cyanoacetate (2.5 q, 20 mmol), was added 10 mg of hydroquione and degassed for 5 minutes at room temperature. Vacuum distillation at pre-warm oil bath (0.2 mbar, oil bath temperature up to 190° C.) was then conducted to afford a colourless oil (Bp: 70-80° C./0.2 mbar, 91% purity, 80% yield). $^1$H NMR (60 MHz, CDCl$_3$): δ 6.97 (s, 1 H), 6.56 (s, 1 H), 6.05-5.60 (br, m, 1 H), 5.42-5.16 (m, 2 H), 4.72 (br, m, 2 H); FT-IR (film): 3127.3, 2237.8, 1735.9, 1649.0, 1617.3, 1389.9, 1283.2, 1185.5, 985.4, 803.5, 713.5 cm$^{-1}$.

Example 15

To a stirring mixture of PRIMENE 81-R iminium-MSA (5.86 g, 20 mmol) and propargyl 2-cyanoacetate (2.46 g, 20 mmol), was added 10 mg of hydroquione and degassed for 5 minutes at room temperature. Vacuum distillation at pre-warm oil bath (0.2 mbar, oil bath temperature up to 200° C.) was then conducted to afford a colourless oil (Bp: 75-85° C./0.2 mbar, 92% purity by CC, 73% yield). $^1$H NMR (60 MHz, CDCl$_3$): δ 7.06 (s, 1 H), 6.65 (s, 1 H), 4.85 (s, 2 H), 2.55 (s, 1 H); FT-IR (film): 3290.2, 3128.8, 2958.2, 2239.7, 2131.7, 1739.7, 1615.1, 1437.6, 1391.1, 1285.4, 1174.5, 990.7, 802.2, 710.9 cm$^{-1}$.

Example 16

To a stirring mixture of PRIMENE 81-R iminium-MSA (5.86 g, 20 mmol) and crotyl 2-cyanoacetate (3.02 q, 20 mmol), was added 10 mg of hydroquione and degassed for 5 minutes at room temperature. Vacuum distillation at pre-warm oil bath (0.2 mbar, oil bath temperature up to 200° C.) was then conducted to afford a colourless oil (Bp: 80-86° C./0.3 mbar, 90% purity by NMR, 65% yield). $^1$H NMR (60 MHz, CDCl$_3$): δ 6.97 (s, 1 H), 6.56 (s, 1 H), 5.72 (m, br, 2 H), 4.60 (m, 2 H), 1.79 and 1.69 (s, s, 3 H); FT-IR (film): 3126.9, 2946.3, 2858.5, 2265.1, 2237.9, 1731.9, 1677.0, 1616.1, 1449.5, 1390.3, 1322.0, 1282.7, 1186.1, 968.9, 804.5, 714.0 cm$^{-1}$.

Example 17

To a stirring mixture of PRIMENE 81-R iminium-MSA (5.86 g, 20 mmol) and cyanoacetate (3.66 g, 20 mmol), was added 10 mg of hydroquione and degassed for 5 minutes at room temperature. Vacuum distillation at pre-warm oil bath (0.2 mbar, oil bath temperature up to 200° C.) was then conducted to afford a colourless oil (90% purity by GC, 58% yield). $^1$H NMR (300 MHz, CDCl$_3$): δ 7.08 (s, 1 H), 6.86 (s, 1 H), 4.29-4.18 (s, 2 H), 3.99 (d, J=13 Hz, 1 H), 3.67-3.59 (m, 1H), 3.50-3.41 (m, 1H), 1.91-1.88 (m, 1H), 1.65-1.51 (m, 4 H), 1.45-1.33 (m, 1 H); $^1$H NMR (75 MHz, CDCl3): δ 160.12, 143.28, 116.20, 114.07, 74.58, 68.92, 68.03, 67.93, 65.92, 21.19, 25.35, 22.57; FT-IR (film): 3124.9, 2942.0, 2852.9, 2237.5, 1738.0, 1614.0, 1442.3, 1388.9, 1320.7, 1287.9, 1190.3, 1095.0, 1078.0, 983.9, 835.5, 803.5, 714.1 cm$^{-1}$.

Example 18

A mixture of PRIMENE 81-R iminium-MSA (5.86 g, 20 mmol) and nitrile malononitrile (1.32 g, 20 mmol), was heated with stirring for a period of time of 1 minute at a temperature of 100° C., after which time vacuum distillation (0.2 mbar, oil bath temperature up to 200° C.) was performed thereon. The distillate was collected as a colourless oil (90% purity, 65% yield). $^1$H NMR (60 MHz, CDCl3): δ 6.85 (s, 2 H).

Example 19

A mixture of PRIMENE 81-R iminium-MSA (5.86 g, 20 mol) and dimethyl malonate (2.64 g, 20 mmol), was heated with stirring for a period of time of 1 minute at a temperature of 100° C., after which time vacuum distillation (0.2 mbar, oil bath temperature up to 200° C.) was performed thereon. The distillate was collected as a colourless oil (50% purity, 50% yield). $^1$H NMR (60 MHz, CDCl$_3$): δ 6.51 (s, br, 2 H), 3.80 (s, 6H).

What is claimed is:

1. A composition of matter comprising structure I:

wherein $R_1$-$R_3$ are each independently selected from the group consisting of H, alkenyl, and alkynyl; X is an anion; and $R_4$ is a hydrocarbon moiety having a tertiary carbon which is attached to the N atom, wherein the tertiary carbon atom is attached to or part of one or more substituents selected from the group consisting of linear, branched, and cyclic alkyl or alkenyl, or one or more together form a cyclic or polycyclic (as the case may be) structure, which itself(themselves) may have substituents attached thereto.

2. The composition of matter of claim 1, wherein the hydrocarbon moiety having a tertiary carbon of $R_4$ is linked to one or more hydrocarbon moieties comprising a tertiary carbon, which moieties themselves may be the same or different and which may be the same or different from the hydrocarbon moiety comprising a tertiary carbon of $R_4$.

3. The composition of matter of claim 1, wherein the hydrocarbon moiety having a tertiary carbon of $R_4$ is substituted with a heterocycle bearing a positive charge to which is associated an anion.

4. The composition of matter of claim 1, wherein the hydrocarbon moiety is substituted with a heteroatom or group of heteroatoms bearing a negative charge to which is associated a cation.

5. The composition of matter of claim 1, wherein the an ionic liquid.

6. The composition of matter of claim 1, which is not distillable at a pressure of 1 mBar and a temperature of 100° C.

7. The composition of matter of claim 1, wherein the composition of matter is in the liquid state at a temperature in the range of −10° C. to +250° C.

8. The composition of matter of claim 1, wherein the composition of matter is in the liquid state at a temperature in the range of 15° C. to +250° C.

9. The composition of matter of claim 1, wherein the composition of matter is in the liquid state at a temperature in the range of 50° C. to +150° C.

10. The composition of matter of claim 1, wherein X of structure I is a non-nucleophilic and/or acidic anion.

11. The composition of matter of claim 1, wherein X of structure I is a member selected from the group consisting of $PF_6$, $BF_4$, $CH_3SO_3$, benzene sulfonate, $AsF_6$, $SbF_6$, $Tf_2N$, $(CN)_2N$, triflate, camphorsulfonate, saccharinate, acesulfamate, $MF_6$, wherein M is a member selected from the group consisting of Nb and Ta, nitrate, $CF_3CO_2$, halide, phosphate, perchlorate, and picrate.

12. The composition of matter of claim 1, wherein X of structure I is a non-nucleophilic and/or acidic anion.

* * * * *